United States Patent [19]

Metcalfe

[11] Patent Number: 4,559,938
[45] Date of Patent: Dec. 24, 1985

[54] ADHESIVE DRESSING AND COMPONENTS

[75] Inventor: Peter J. Metcalfe, Bishops Stortford, United Kingdom

[73] Assignee: Smith and Nephew Associated Companies p.l.c., Great Britain

[21] Appl. No.: 406,988

[22] Filed: Aug. 11, 1982

[30] Foreign Application Priority Data

Aug. 12, 1981 [GB] United Kingdom ............... 8124649

[51] Int. Cl.$^4$ .............................................. B32B 3/26
[52] U.S. Cl. .................... 128/156; 428/220;
428/315.5; 264/41; 525/232
[58] Field of Search ............... 128/155, 156; 604/370, 604/372; 521/100, 102; 428/315.5; 525/232; 264/41, DIG. 47

[56] References Cited

U.S. PATENT DOCUMENTS

| 3,426,754 | 2/1969 | Bierenbaum | 604/897 |
| 3,801,692 | 4/1974 | Zimmerman | 264/154 |
| 3,932,682 | 1/1976 | Loft et al. | 428/315.5 |
| 4,133,310 | 1/1979 | Lloyd et al. | 128/156 |
| 4,135,021 | 1/1979 | Patchell et al. | 604/370 |

FOREIGN PATENT DOCUMENTS 1454870 11/1976 United Kingdom .
2081721 5/1984 United Kingdom .

OTHER PUBLICATIONS

Journal of the Plastics Institute Conference Supplement No. 3, Seymour, et al.
JSR RB Technical Information Booklet, p. 1.

Primary Examiner—C. Fred Rosenbaum
Assistant Examiner—Sherri E. Vinyard
Attorney, Agent, or Firm—Jacobs & Jacobs

[57] ABSTRACT

A flexible film suitable for use in adhesive medical dressings which film comprises a blend of polymers characterized in that the blend comprises a continuous matrix of 1,2 polybutadiene and an incompatible polymer which forms a discrete particulate phase within the continuous matrix and the film contains voids is described.

16 Claims, No Drawings

ADHESIVE DRESSING AND COMPONENTS

The present invention relates to adhesive medical dressings, flexible films therefor and methods of manufacture thereof.

Adhesive medical dressings such as first aid dressings should be conformable to skin to enable the dressing to remain comfortably adhered to the patient. Such dressings should therefore have a flexible backing film. Conventional plasticised polyvinyl chloride films have the disadvantage that migration of the plasticiser from the film into the adhesive layer can result in deterioration of the adhesive. Conventional unplasticised flexible films tend to lack the necessary conformability to skin. British Patent Specification No. 2081721A (unpublished at the date of filing British Patent Application No. 8124849 from which the present application claims priority) disclosed that blends of polyurethane and an incompatible polymer could be employed as backing films for adhesive dressings. It would be desirable to provide an alternative to polyurethane blend films which could employ another and preferably cheaper polymer in place of the polyurethane. Such a conformable film suitable for use in an adhesive dressing has now been discovered.

The present invention provides a flexible film suitable for use as a backing in an adhesive medical dressing which film comprises a blend of polymers characterised in that the blend comprises a continuous matrix of 1,2 polybutadiene and an incompatible polymer which forms a discrete particulate phase within the continuous matrix and the film contains voids.

The present invention also provides an adhesive medical dressing comprising a flexible film backing and an adhesive layer characterised in that the film comprises a blend of polymers characterised in that the blend comprises a continuous matrix of 1,2 polybutadiene and an incompatible polymer which forms a discrete particulate phase within the matrix and the film contains voids.

The term "voids" when used herein means small holes within the film. These small holes may interrupt the surface or may coalesce. Normally most of the voids have a diameter from 3 to 20 microns, for example 3 to 6 microns. Continuous voided films of this invention are impermeable to liquid water and therefore do not contain openings or passages which provide a continuous pathway through the film material. This therefore allows the film material to act as a bacterial barrier when this is desired. The discrete particulate phase is normally located within the voids in the film.

The conformability of the film of this invention is believed to result from the presence of the continuous matrix of the 1,2 polybutadiene and the increase in moisture vapour transmission is believed to result from the presence of the voids.

Suitable 1,2 polybutadiene blend films of this invention have a thickness of 25 microns to 250 microns (i.e. 0.025 mm to 0.25 mm) and preferably have a thickness of 50 microns to 150 microns. Films of this invention of such thickness have the conformability particularly suitable for use as dressings.

It has been found that the most suitable 1,2 polybutadienes for use in this invention are thermoplastic 1,2 polybutadienes. Favoured thermoplastic 1,2 polybutadienes for making films of this invention contain a major amount of syndiotactic 1,2 polybutadiene, have a crystallinity of 15% to 30% (for example 25% to 30%) and have a weight average molecular weight in excess of 100,000.

Preferred 1,2 polybutadienes for use in this invention are known as RB 810, RB 820 and RB 830 made by Japan Synthetic Rubber Company. The 1,2 polybutadiene may contain other materials such as antioxidants and fillers but is preferably unfilled. The 1,2 polybutadiene may be crosslinked but is preferably uncrosslinked.

In films of this invention the incompatible polymer forms a discrete particulate phase within a continuous matrix of the 1,2 polybutadiene. It is preferred that the particles of the discrete particulate phase of incompatible polymer should be spherical or ellipsoidal in shape and have a diameter of at least 1 micron, for example 2 microns to 6 microns.

It is desirable that the 1,2 polybutadiene blend films of this invention be adapted to have a recoverable elastic strain of at least 50% and preferably at least 100%

The films of the invention are opaque due to voids in the body of the film.

Suitable incompatible polymers include those derived from polymerisation of vinyl hydrocarbons, for example polystyrene and other polyolefins such as polyethylene and polypropylene. It has been found that polystyrene is a particularly suitable incompatible polymer for use with 1,2 polybutadiene.

It is desirable that mechanical and physical properties of the incompatible polymer are significantly different from that of the 1,2 polybutadiene at temperatures at which the film will stretch. It is particularly desirable that the incompatible polymer should have a higher modulus than that of the 1,2 polybutadiene at cold stretch temperatures. It is also desirable that the incompatible polymer has a lower melt viscosity than the 1,2 polybutadiene at its melt forming temperature.

An especially suitable incompatible polymer is polystyrene. The polystyrene may be an unmodified grade (homopolymer) or rubber modified grade. High impact polystyrene (rubber modified grade) is a preferred incompatible polymer.

A particularly preferred polystyrene is a high impact polystyrene reference 6MW supplied by R. H. Cole Limited.

The proportions of 1,2 polybutadiene and the incompatible polymer depend to some extent on the individual polymers. However, in general the blends of this invention suitably contain 40% to 90% by weight, desirably 45% to 85% by weight and preferably 50% to 80% by weight of 1,2 polybutadiene.

A preferred blend contains 60% by weight of 1,2 polybutadiene (for example RB 830 from Japan Synthetic Rubber Co.) and 40% by weight of high impact polystyrene (for example 6MW from R. H. Cole Limited). Another preferred blend contains 75% by weight of 1,2 polybutadiene and 25% by weight of high impact polystyrene.

The adhesive dressing of the invention are preferably moisture vapour transmitting, for example will transmit at least 100 g/m$^2$. Suitable adhesive dressings will be adapted to have a moisture vapour transmitting rate of at least 200 g/m$^2$, desirably at least 300 g/m$^2$ and preferably 500 g/m$^2$ at 37° C. at 100% to 10% relative humidity difference (24 hour figures). By employing voided films of this invention higher moisture vapour transmission can be achieved than by employing 1,2 polybutadiene alone. However if particularly high moisture vapour transmissions are required a discontinuous film may be employed as described hereinafter.

When used as a backing film for adhesive medical dressings of the invention it is preferred that the 1,2 polybutadiene blend film has a moisture vapour transmission rate of at least 300 g/m$^2$ and preferably at least 500 g/m$^2$.

The moisture vapour transmission rate may be measured by the Payne Cup method. The method uses a cup 1.5 cm deep with a flanged top. The inner diameter of the flange is such to provide an area for mositure vapour transmission of 10 cm$^2$. In this method 10 ml. of distilled water is added to the cup and a sample of the material under test, large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed as in g/m$^2$/24 hrs. at 37° C. at 100% to 10% relative humidity difference.

In moisture vapour transmitting adhesive dressings of the invention either or both of the 1,2 polybutadiene blend backing film and the adhesive layer can be discontinuous.

The discontinuous 1,2 polybutadiene blend films will contain apertures. The apertures can be of any suitable shape such as circles, rectangles, ellipses and like shapes. The size of the apertures can be suitably from 0.2 mm to 0.1 mm and will preferably be from 0.4 mm to 0.5 mm in diameter. Generally the apertures will comprise 0.5 to 20% of the area of the film and more usually 1 to 10% of the area of the film.

In adhesive dressings of the invention the apertures in 1,2 polybutadiene film will normally be in a uniform pattern. The apertures will usually be over substantially the whole area of the film or alternatively the apertures can be limited to an area of the film such as an area adjacent to an intended wound contacting area of the dressing such as an absorbent pad in dressings which have such pads.

The adhesive layer in the moisture vapour transmitting adhesive dressings of the invention can be continuous or discontinuous. Discontinuous adhesive layers include porous (including microporous) and pattern layers. The adhesive layer can be in a pattern of dots or parallel lines but preferred patterns are a square grid or diamond pattern for example as disclosed in British Patent Specification No. 819,635.

Suitable discontinuous adhesive layers can comprise any non-toxic, skin adhering pressure sensitive adhesive. Favoured adhesives include acrylate ester copolymer and polyvinyl ethyl ether adhesives.

Suitable continuous adhesive layers can comprise any moisture vapour permeable adhesive such as an acrylate ester copolymer or a polyvinyl ether such as ethyl polyvinyl ether. Preferred acrylate ester copolymer adehsives are disclosed in United Kingdom Application No. 8106707. A favoured acrylate ester copolymer consists of 47 parts by weight of 2-ethylhexyl acrylate, 47 parts by weight of n-butyl acrylate and 6 parts by weight of acrylic acid.

Suitably the thickness of the adhesive layer of adhesive dressings of the invention is from 12.5 to 75 microns and is preferably from 20 to 50 microns, for example 22 to 30 microns.

The adhesive dressings of the invention can be first aid dressings, medium size wound dressings for example 7.5 cm×5 cm or ward dressings. Such dressings will often contain a pad which is preferably covered with a non-adherent wound facing layer. The adhesive dressing of the invention may also be in the form of an adhesive tape. The adhesive layer of the dressing of the invention can have a conventional peelable protector covering its exposed surface. The adhesive dressings of the invention can be sterile within a suitable bacteria proof package.

In a further aspect the invention provides a process of making adhesive medical dressings of the invention which comprise applying an adhesive layer to a flexible film comprising a blend of 1,2 polybutadiene and an incompatible polymer and contains voids.

In yet another aspect the invention provides a process of making the film of the invention which comprises forming a film from a blend of 1,2 polybutadiene and an incompatible polymer and stretching the film until voiding occurs. Thereafter the stretched film is allowed to contract.

It is preferred that the film is formed by a hot melt process in particular by hot melt extrusion. It is also preferred that the blending of the 1,2 polybutadiene and the incompatible polymer is carried out under hot melt conditions although pre-mixing of the granules can be carried out by tumbling at room temperature.

The extruded 1,2 polybutadiene and incompatible polymer blend film can be stretched to form the flexible film containing voids. The stretching should be carried out at low temperatures for example 10° C. to 45° C. preferably at 15° C. to 30° C. The stretching can take place in longitudinal or transverse to the extrusion direction. It is preferred that the film should be given a stretch of between 200% and 500%. The degree of stretching should be greater than the yield elongation (but less than the elongation at break of the film) at the stretching temperature.

The films of this invention may be prepared by the process of British Patent Specification No. 8124250 which is incorporated herein.

Essentially the films are prepared by blending the ingredients, extruding a film and stretching it. After stretching the film is also allowed to contract. These stretching and relaxation stages convert the 1,2 polybutadiene-incompatible blend films into a flexible film containing voids. These voids are normally very small with diameters of between 2 and 20 microns and more usually between 3 and 16 microns.

The adhesive layer can be applied to the flexible film by conventional coating methods using for example blade over flat bed or roller coating units. The adhesive can be applied directly to the flexible film as an emulsion or as a solution providing the solvent or solvents used are selected from those which do not significantly dissolve or swell the film. Alternatively the adhesive can be applied in a solventless form for example as a polymerisable monomer or prepolymer mixture.

Patterned adhesive layers can be applied to the flexible film using an engraved roller by the method disclosed in British Patent Specification No. 819,635.

In a preferred process the adhesive is applied to the flexible film by a transfer process in which the adhesive is coated onto a release surface such as a silicone coated paper and transferred to the film by laminating the film to the adhesive coated release surface under pressure.

The flexible 1,2 polybutadiene blend film can be provided with apertures by conventional perforating methods including methods involving the use of punches and dies, heated needles or protruberances, hot gases and elextrical spark discharge. Adhesive coated film can be provided with suitable apertures in a similar manner.

The adhesive coated film can be converted into medical adhesive dressings on conventional machines, for example dressing machines.

The adhesive medical dressings can be individually wrapped in bacteria proof packages. The packaged dressings can be sterilised by a conventional sterilising method such as electron or gamma irradiation or ethylene oxide sterilisation.

EXAMPLES 1 TO 8

Preparation of 1,2 polybutadiene Blend Film

The effect of the processing conditions on the moisture vapour transmission rates of voided films made from polymer blends of 1,2 polybutadiene(PBD) reference RB 830 (Japan Synthetic Rubber Co,) and high impact polystyrene (HIPS) reference 6MW (from R. H. Cole Limited) are illustrated by Examples 1 to 8.

The voided films of Examples 1 to 8 were made by extruding a polymer mixture as a hot melt through a flat film die into a cooled two roller casting unit and stretching the resultant film on a laboratory tensometer in the following manner.

Polymer Mixture Preparation (a) Granules of the 1,2 polybutadiene and the incompatible polymer were mixed by tumbling.

(b) The polymer prepared was then dried in an air circulating oven at 90° C. for 4 hours using 2.5 cm deep trays.

Extrusion conditions

Films were made by feeding the polymer mixture into a 375 mm extruder (Johnson Spartan 150, length to diameter screw ratio of 24:1) and extruding the polymer mixture at a melt temperature of 185° C. through a 300 mm flat film die into the nip of a cooled two roller film casting unit located 7.5 cm directly below the die (rollers maintained at 40° C. and 30° C.).

Stretching conditions

The voided films were made by stretching samples of the cast film in the machine direction (M) on a laboratory Hounsfield tensometer. The film samples had a gauge length of 50 mm and an aspect ratio of 0.5. Samples were stretched to a draw ratio of 5:1 (400% extension) at rates of between 50 mm/min and 125 mm/min at 20° C. and 25° C.

Results

The properties of the thus produced films are given in Table 1. The moisture vapour transmission rate (MVTR) was calculated by the Payne Cup method.

The results show that the MVTR of the voided films is greater than that of films of similar thickness composed of 1,2 polybutadiene alone. (MVTR of about 90 g/m$^2$/24 hrs/37° C./100% to 10% relative humidity difference for 100 micron film).

TABLE 1

| | Processing Details | | Film Properties | | Initial | Final | | | |
|---|---|---|---|---|---|---|---|---|---|
| Example No. | Screw Speed (revs/min) | Casting Speed | Initial thickness (mm) | Final Thickness (mm) | weight per unit area (g/m$^2$) | Weight per unit area (g/m$^2$) | MVTR | Composition % by weight | |
| | | | | | | | | PBD | HIPS |
| 1 | 22.5 | 2 | 0.16 | 0.11 | 150 | 79 | 294 | 60 | 40 |
| 2 | 22.5 | 4 | 0.08 | 0.055 | 77 | 36 | 320 | 60 | 40 |
| 3 | 37.5 | 4 | 0.135 | 0.08 | 124 | 56 | 253 | 60 | 40 |
| 4 | 37.5 | 2 | 0.265 | 0.173 | 250 | 127 | 207 | 60 | 40 |
| 5 | 37.5 | 2 | 0.245 | 0.143 | 231 | 119 | 106 | 75 | 25 |
| 6 | 37.5 | 4 | 0.135 | 0.078 | 125 | 64 | 155 | 75 | 25 |
| 7 | 22.5 | 4 | 0.088 | 0.048 | 79 | 36 | 205 | 75 | 25 |
| 8 | 22.5 | 2 | 0.168 | 0.095 | 155 | 86 | 128 | 75 | 25 |

EXAMPLE 9

Preparation of Adhesive Dressings

The film of Example 2 was coated with a pressure sensitive adhesive composition consisting of a copolymer of 47 parts by weight of 2-ethylhexyl acrylate, 47 parts by weight of n-butyl acrylate and 6 parts by weight of acrylic acid polymerised in acetone according to the general method of United Kingdom Application No. 8106707 to give a dry continuous adhesive layer of about 25 g/m$^2$. The film was coated by a transfer process in which the adhesive solution was coated (knife over flat bed coating unit) onto a release paper (Steralease 77 from Sterling Coated Papers Limited) and then transferred to the film by lamination under pressure.

The adhesive coated film was converted into first aid dressings on a conventional dressing machine.

The dressings were found to conform well to the skin when applied to the hands of volunteers.

EXAMPLE 10

Extrusion Compound Preparation

An extrusion feedstock was prepared as follows:

(i) 60 parts by weight of polybutadiene polymer granules were combined with 40 parts by weight of high impact polystyrene (HIPS) granules (Styron 485, manufactured by the Dow Chemical Co. Ltd., and supplied by R. H. Cole Ltd., reference 6MW) and the resultant mixture introduced into a rotary tumble blender, which was operated for ten minutes to ensure that a sufficiently even dispersion of one type of granule in the other had been obtained for the efficient operation of the next stage of the process.

(ii) The mixture of granules from (i) was loaded into the hopper of a Reifenhauser S60 60 mm extruder. This extruder was equipped with a multirod die which had 12 circular outlet channels, each 3 mm in diameter. The extruder was also equipped with a polyolefin type screw which had a length to diameter ratio of 20:1 and a compression ratio of 3:1.

The extrusion was carried out using a die temperature of 185° C. and a screw speed of 38 rpm. The filaments produced were drawn through a water bath maintained at 20° C. at a speed sufficient to reduce their diameters to approximately 2 mm. After travelling a distance of 1 meter through this bath the filaments were passed through a chamber equipped with a hot air blower, to remove excess moisture before being cut into 3 to 5 mm lengths using an Accrapak model laboratory granulator.

The granules were collected from the granulator and then dried for four hours at 90° C. in an air circulating oven in trays 2.5 cm deep.

Film Extrusion

The compound was fed into the hopper of a Brabender Extrusiograph instrumented extruder, which was driven by a Brabender Plasticorder PLE 651 drive unit and which was equipped with a 25 mm diameter tubular blown film die and a polyolefin-type screw with a length to diameter ratio of 25:1 and compression ratio of 3:1. The die was maintained at a temperature of 185° C. and, using a screw speed of 60 rpm, which gave registered torque and axial back pressure measurements of 31 Nm and 1 Kn respectively, a melt film was extruded vertically and fed into the nip of a haul off unit located 65 cm above the die face.

Stretching Conditions

A voided film was made by stretching a sample of the film in the machine direction (M) on a laboratory Hounsfield tensometer. The film sample had a gauge length of 50 mm and an aspect ratio of 0.5. Samples were stretched to a draw ratio of 5:1 (400% extension) at a rate of 50 mm/minute at 20° C.

Results

The film reduced in thickness from 1.47 mm to 0.64 mm and the drawn film had an MVTR of 280 g/m$^2$/24 hr. The initial modulus of the drawn film, determined by measuring the slope of the load/elongation curve, was 40 MPa. This was measured using an Instron 1195 tensile testing machine. The sample width was 25 mm and the gauge length was 25 mm. For comparison the corresponding value for a typical continuous polyvinyl chloride substrate film is 87 MPa.

EXAMPLE 11

Preparation of Adhesive Dressings

The film of Example 10 was coated with a pressure sensitive adhesive composition as described in Example 9 except that prior to coating, the film was perforated mechanically to give a series of circular perforations 1 mm in diameter such that the area of the perforations was approximately 1.5% of the film area. The MVTR of the coated film was 327 g/m$^2$/24 hr.

The adhesive coated film was converted into first aid dressings on a conventional dressing machine, The dressings were found to conform well to the skin when applied to the hands of volunteers.

I claim:
1. A flexible film suitable for use in adhesive medical dressings which film comprises a blend of polymers which comprises a continuous matrix of 1,2 polybutadiene and an incompatible polymer which forms a discrete particulate phase within the continuous matrix and the film contains voids whereby said voids provide means for moisture vapor transmission but not liquid permeability.
2. A film according to claim 1 which is 50 microns to 150 microns thick and in which the voids have a diameter of 3 to 20 microns.
3. A film according to claim 1 in which the incompatible polymer is polystyrene.
4. A film according to claim 1 in which the 1,2 polybutadiene comprises 45% to 80% by weight of the film.
5. A film according to claim 1 which is adapted to have a moisture vapour transmission rate of at least 200 g/m$^2$/24 hours/37° C./100% to 10% relative humidity difference.
6. A film according to claim 1 which has apertures and has a moisture transmission rate of at least 500 g/m$^2$/24 hours/37° C./100% to 10% relative humidity difference.
7. An adhesive medical dressing which comprises a flexible backing film of claim 1 on which is disposed an adhesive layer.
8. An adhesive medical dressing according to claim 7 in which the adhesive layer is a continuous layer of moisture vapour permeable adhesive.
9. An adhesive dressing according to claim 7 in sterile form and within a bacteria-proof package.
10. A process for preparing a flexible voided film according to claim 1 which comprises forming a film from a blend of 1,2 polybutadiene and an incompatible polymer and stretching the film until the voids are formed.
11. A film according to claim 1 wherein the 1,2 polybutadiene is a thermoplastic 1,2 polybutadiene.
12. A film according to claim 11 wherein the thermoplastic 1,2 polybutadiene contains a major amount of syndiotactic 1,2 polybutadiene having a crystallinity of 15% to 30% and an average molecular weight in excess of 100,000.
13. A film according to claim 1 wherein the particles of the discrete particulate phase of incompatible polymer are spherical or ellipsoidal in shape and have a diameter of at least 1 micron.
14. An adhesive medical dressing which comprises a flexible backing film of claim 11 on which is disposed an adhesive layer.
15. An adhesive medical dressing which comprises a flexible backing film of claim 12 on which is disposed an adhesive layer.
16. An adhesive medical dressing which comprises a flexible backing film of claim 13 on which is disposed an adhesive layer.

* * * * *